United States Patent [19]

Pietralla et al.

[11] 4,294,771
[45] Oct. 13, 1981

[54] METHOD FOR THE PRODUCTION OF METAL SOAPS

[76] Inventors: Norbert Pietralla, Weidenstrasse 33, 8034 Unterpfaffenhofen; Valentin Ausserbauer, Zugspitzweg 29, 8015 Markt Schwaben; Christian Rosenthal, Bäckergasse 15, 8131 Berg, all of Fed. Rep. of Germany

[21] Appl. No.: 134,194

[22] Filed: Mar. 27, 1980

[30] Foreign Application Priority Data

Apr. 4, 1979 [DE] Fed. Rep. of Germany ....... 2913592

[51] Int. Cl.$^3$ ........................................... C08H 17/36
[52] U.S. Cl. ..................................... 260/413; 260/414
[58] Field of Search ............................ 260/413 S, 414

[56] References Cited

U.S. PATENT DOCUMENTS 3,803,188  4/1974  Scott et al. .......................... 260/414
4,060,535  11/1977  Cinco .................................. 562/598

*Primary Examiner*—John F. Niebling
*Attorney, Agent, or Firm*—Scully, Scott, Murphy & Presser

[57] ABSTRACT

The invention relates to a method for producing metal soaps by reacting aliphatic carboxylic acids with metal oxides, metal hydroxides and/or metal carbonates, wherein the metal soaps are directly obtained in the form of granulates without requiring an additional granulating step.

7 Claims, No Drawings

METHOD FOR THE PRODUCTION OF METAL SOAPS

This invention relates to a method for the production of metal soaps or metal soap mixtures by reacting at least one aliphatic carboxylic acid having about 8 to 22 carbon atoms with at least one metal oxide and/or hydroxyde and/or carbonate in the presence of water at elevated temperature by agitation, and subsequent removal of the water.

Known already is a method wherein a metal soap is obtained by a two-step reaction of the carboxylic acid. A first reaction with an equivalent amount of sodium hydroxide solution or potassium hydroxide solution results in the respective alkali soap. In a further step, this alkali soap is mixed with a selected metal salt, and the resulting insoluble metal soap is precipitated. This reaction takes place at temperatures between 60° and 70° C. in an excess amount of water about twenty times that of the carboxylic acid employed. Separation of the precipitated metal soap may be carried out for instance by filtration or centrifugation. The proportion of the also formed alkali salt is reduced to less than 1% by washing, whereupon the metal soap is dryed and ground. The end product is obtained in a very low-density, voluminous form and, what has to be considered as particularly disadvantageous, gives off large amounts of dust. A further disadvantage of this method is the requirement of numerous and involved process steps.

In a further known method, the reaction of the carboxylic acid with the respective metal oxide, hydroxide or carbonate is carried out in the molten condition. In this method, the metal oxide, hydroxide or carbonate is added to the molten carboxylic acid at a temperature lying above the melting point of the expected end product, and the forming reaction and hydrate water is removed by evaporation. The anhydrous melt is subsequently solidified by the employ of cooling towers, cooling cylinders or cooling baths and is then ground. A disadvantage of this method is that it also results in dusty and relatively dark-coloured end products. Further processing of these products is additionally hampered particularly due to its coarse grain and the unsatisfactory distribution resulting therefrom.

Described in DE-AS No. 10 68 238 is a further method for producing lead salts of fatty acids. According to this method, the reaction of the fatty acid in particulate or finely distributed form with lead oxide is carried out in aqueous suspension at temperatures slightly below the melting temperature of the acid. The resulting insoluble lead soap is drawn off and subsequently dryed. A disadvantage of this method again resides in the great amount of water required for obtaining the requisite fine distribution of the fatty acid in aqueous suspension, this water amount corresponding to about six to thirteen times to the amount of the employed carboxylic acid. This method does not either lead directly to an end product in granulate form.

It is an object of the present invention to provide an improved method for the production of metal soaps or metal soap mixtures, which is free of the disadvantages of known methods and leads directly to metal soaps or metal soap mixtures in substantially dust-free granulate form in a simple and economical manner without an additional process step.

In order to attain this object in a method as set forth in the introduction, the invention provides the steps of adding 1 to 5% of water, as referred to the total weight of the carboxylic acid(s), heating the mixture to a temperature required for initiating the reaction, causing the exothermic reaction to proceed within a sealed pressure reactor without further supply of external heat, subsequently reducing the built-up over-pressure and drawing off the water contained in the reaction mixture at reduced pressure.

The method according to the invention offers the following advantages over known methods:

A particular disadvantage of the known methods is to be seen in the fact that the end products are obtained with a high dust content, and are frequently of dark coulour.

The method according to the invention surprisingly leads directly to end products in granulate form. These products do therefore not give off any substantial amount of dust and show improved properties as compared to metal soaps obtained by two-step reaction in the aqueous phase or direct reaction in the molten state.

The grain size distribution of the end products obtained in granular form by the method according to the invention is extraordinarily favourable, inasmuch as about 80% of the total amount lie within the desired particle size range. It is thus for instance possible according to the invention to obtain a product in which about 80% of the metal soap lie within a particle size range of between 0.2 and 2 mm.

A further advantage of the method according to the invention over known methods resides in the fact that it is energy-saving and thus more economical than the known methods during the reaction itself as well as during the subsequent drying step. This is due to the fact that the known methods required the additional heating of the twentyfold amount of water, as referred to the employed amount of carboxylic acid, and that drying of the metal soap in the method according to the invention does not require any additional energy input, since the amount of heat contained in the reactor contents is sufficient to completely evaporate the water on evacuation of the reactor.

Furthermore, in the above described known two-step reaction method, drying of the metal soaps is carried out by conventional drying techniques (e.g. by means of belt dryers, fluid flow dryers, tray dryers, drum dryers or cascade dryers), resulting in environmant pollution by the release of minute dust particles.

According to the method of the invention, the production of the metal soap or metal soap mixture from the reaction step up to the final end product is carried out in a closed container, and is thus simpler and less timeconsuming than conventional methods.

An advantageous embodiment of the method according to the invention is carried out as follows:

An aliphatic carboxylic acid having about 8 to 22 carbon atoms and/or a mixture of such carboxylic acids is mixed within a pressure reactor with at least one metal oxide and/or hydroxide and/or carbonate, with the addition of 1 to 5% water, as referred to the total weight of the carboxylic acid(s), the mixture being then heated to a temperature required for initiating the reaction. The mixture is agitated while the exothermic reaction proceeds at a temperature between about 90° and 110° C., resulting in the build-up of a pressure of about 1.1 to 1.3 bar over a period of about 10 to 15 minutes. After completion of the reaction, the built-up pressure is decreased, and the added water as well as the resulting reaction water is drawn off under decreased pressure conditions and preferably increased agitation speed. This results in the temperature of the reaction product dropping relatively rapidly to about 50° to 55° C., whereby an end product is obtained in granulate form. The obtained granulate is fractioned over a sieve, and the undesirable coarse and fine fractions, which amount to only about 10% of the total amount, are returned to the following reaction mixture.

In the method according to the invention, the added amount of water is preferably 2 to 4% of the total weight of the carboxylic acid(s), since these proportions lead to optimum results.

Initiation of the exothermic reaction in the method according to the invention requires an initial activating energy input in the form of heat. In this context it has been found to be particularly advantageous to heat the mixture at least to the melting point of the employed carboxylic acid, or at least to the melting range of the employed carboxylic acid mixture, i.e. generally to a temperature of about 50° to 60° C.

The employed aliphatic carboxylic acids having about 8 to 22 carbon atoms are preferably selected from straightchain carboxylic acids optionally containing hydroxyl groups.

In order to obtain a white end product, the method according to the invention preferably employs at least one oxide and/or hydroxide and/or carbonate of a metal selected from the group including lithium, sodium, potassium, magnesium, calcium, strontium, barium, tin, lead, and zinc. It is also possible, however, to employ oxides and/or hydroxides and/or carbonates of metals selected from the group including copper, iron, nickel, maganese and chromium, metal soaps produced with these are cloloured, however, and therefore generally less preferred.

The employed amount of the metal oxide and/or hydroxide and/or carbonate is preferably at least equivalent to that of the acid. More preferably, one employs a slight excess of about 2% over the amount of at least one metal oxide and/or hydroxide and/or carbonate which is equivalent to the acid amount in order to prevent the presence of undesired free acid groups after the reaction.

If the metal soaps produced by known methods were required to be obtained in granulate form, a further process step was required in which the metal soaps had to be granulated in high-speed mixing or forming devices with the addition of granulating additives at temperatures above the melting point of such additives, followed by cooling and sieving. With the method according to the invention, however, one obtains soft, readily flowing and easily metered granulates in a straightforward manner. If desired, the thus obtained metal soap granulates can be coated for instance with known lubricants conventionally employed as granulating additives, such as paraffins of fats, in one and the same reactor after the water has been drawn off.

Embodiments of the invention shall now be described in detail by the following examples:

EXAMPLE 1

Production of a calcium soap 25 kg of a technical carboxylic acid mixture having the chain length $C_{14}$ to $C_{20}$ (2% $C_{20}$, 64% $C_{18}$, 2% $C_{17}$, 28% $C_{16}$, 4% $C_{14}$) and an average molecular weight of 273 are introduced into a pressure reactor provided with a stirrer and having a capacity of 130 liters, together with 0.5 liter of water and 3.5 kg calcium hydroxide. The mixture is heated to 50° to 60° C., whereupon the reaction proceeds exothermic without further heat input. The reaction is carried out under agitation of the mixture, the pressure in the sealed reactor rising to 1.1 to 1.3 bar. When the pressure, or the temperature, respectively, starts to decrease, the reaction is completed. The reactor is then evacuated, and the water content is drawn off under further agitation and decreased pressure. The directly obtained end product is a dust-free calcium soap in granulated, freely flowing form with a narrow grain size range.

The following examples are carried out in the same manner as Example 1.

EXAMPLE 2

Production of a lead soap 25 kg of the same carboxylic acid mixture as in Example 1 are reacted with 0.5 liters of water and 10.6 kg lead oxide.

EXAMPLE 3

Production of a zinc soap 25 kg of the same carboxylic acid mixture as in Example 1 are reacted with 0.5 liter of water and 3.75 kg zinc oxide.

EXAMPLE 4

Production of a barium-cadmium soap 25 kg of a technical carboxylic acid mixture having the chain length $C_{10}$ to $C_{14}$ (1% $C_{10}$, 93% $C_{12}$, 6% $C_{14}$) and an average molecular weight of 200 are reacted with 0.5 l water, 4.0 kg cadmium oxide and 5.4 kg barium hydroxide.

EXAMPLE 5

Production of a barium-cadmium soap 25 kg of the same carboxylic acid mixture as in Example 1 are reacted with 0.5 l water, 2.95 kg cadmium oxide and 2.95 kg barium hydroxide.

EXAMPLE 6

Production of a sodium soap 30 kg of the same carboxylic acid mixture as in Example 1 are reacted with 0.5 l water and 4.4 kg sodium hydroxide (100% pure).

EXAMPLE 7

Production of a barium soap 30 kg of the same carboxylic acid mixture as in Example 1 are reacted with 0.5 l water and 9.5 kg barium hydroxide.

The products obtained in Examples 2 to 7 were likewise dust-free metal soaps in a freely-flowing granulate form.

What is claimed is:

1. In a process for producing granulate metal soap or metal soap mixture in which at least one aliphatic carboxylic acid having about 8 to 22 carbon atoms is reacted with at least one soap-forming metal compound selected from the group consisting of metal oxide, metal hydroxide and metal carbonate in the presence of water at elevated temperature to provide soap, and water is subsequently removed, the improvement which comprises:

(a) heating a reaction mixture containing carboxylic acid and soap-forming metal compound in the presence of from 1 to 5 weight percent water based on the total weight of carboxylic acid(s) to a temperature at which the soap-forming reaction is initiated;
(b) permitting the soap-forming reaction to proceed under built-up overpressure without further supply of external heat;
(c) reducing the built-up overpressure; and,
(d) removing water from the reaction mixture under reduced pressure to provide granulate metal soap or metal soap mixture.

2. A method according to claim 1 wherein the reaction of carboxylic acid and soap-forming metal compound takes place in the presence of from 2 to 4 weight percent water based on the total weight of the carboxylic acid(s).

3. A method according to claim 1 wherein the reaction is initiated by heating the mixture at least to the melting point of the employed carboxylic acid, or at least to the melting range of the employed carboxylic acid mixture, respectively.

4. A method according to claim 1 wherein the carboxylic acid(s) having about 8 to 22 carbon atoms employed is, or are, respectively, selected from the group consisting of straightchain and hydroxyl-group-containing carboxylic acids.

5. A method according to claim 1 wherein the metal of the soap-forming metal compound is selected from the group consisting of lithium, sodium, potassium, magnesium, calcium, cadmium, strontium, barium, tin, lead, and zinc.

6. A method according to claim 1 wherein the amount of soap-forming compound used is at least equivalent to the acid.

7. A method according to claim 1 wherein the soap-forming compound is employed slightly in excess by about 2% of an amount equivalent to the carboxylic acid.

* * * * *